United States Patent
Naito et al.

(10) Patent No.: US 12,419,603 B2
(45) Date of Patent: Sep. 23, 2025

(54) RADIATION IMAGING APPARATUS, RADIATION IMAGING SYSTEM, METHOD, AND NON-TRANSITORY STORAGE MEDIUM

(71) Applicant: CANON KABUSHIKI KAISHA, Tokyo (JP)

(72) Inventors: Yuichi Naito, Kanagawa (JP); Hiroki Asai, Kanagawa (JP); Hideyuki Okada, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 181 days.

(21) Appl. No.: 18/516,748

(22) Filed: Nov. 21, 2023

(65) Prior Publication Data
US 2024/0173006 A1 May 30, 2024

(30) Foreign Application Priority Data
Nov. 25, 2022 (JP) .................. 2022-188490

(51) Int. Cl.
| | | |
|---|---|---|
| *A61B 6/00* | (2024.01) | |
| *A61B 6/08* | (2006.01) | |
| *A61B 6/58* | (2024.01) | |
| *G01J 5/08* | (2022.01) | |
| *G01J 5/00* | (2022.01) | |

(52) U.S. Cl.
CPC .............. *A61B 6/586* (2013.01); *A61B 6/08* (2013.01); *A61B 6/54* (2013.01); *A61B 6/56* (2013.01); *G01J 5/0859* (2013.01); *G01J 2005/0077* (2013.01)

(58) Field of Classification Search
CPC ......... A61B 1/00; A61B 1/00112; A61B 6/10; A61B 6/102; A61B 6/40; A61B 6/54; A61B 6/548; A61B 6/56; A61B 6/58; H04N 23/66; H04N 23/661; H04N 23/665; H04N 23/667
See application file for complete search history.

(56) References Cited

U.S. PATENT DOCUMENTS

2022/0117574 A1\* 4/2022 Miyake ................ A61B 6/5205

FOREIGN PATENT DOCUMENTS

| JP | 2002277993 A | 9/2002 |
|---|---|---|
| JP | 2004357762 A | 12/2004 |
| JP | 2009034428 A | 2/2009 |
| JP | 2019526424 A | 9/2019 |

\* cited by examiner

*Primary Examiner* — Don K Wong
(74) *Attorney, Agent, or Firm* — Canon U.S.A., Inc. IP Division

(57) ABSTRACT

A radiation imaging apparatus for use in a radiation imaging system including a radiation source and a camera includes one or more controllers that acquire state information of the radiation imaging apparatus and perform, in response to acquisition of state information corresponding to an abnormality of the radiation imaging apparatus, communication to cause the camera to perform image capturing on a range including the radiation imaging apparatus.

13 Claims, 7 Drawing Sheets

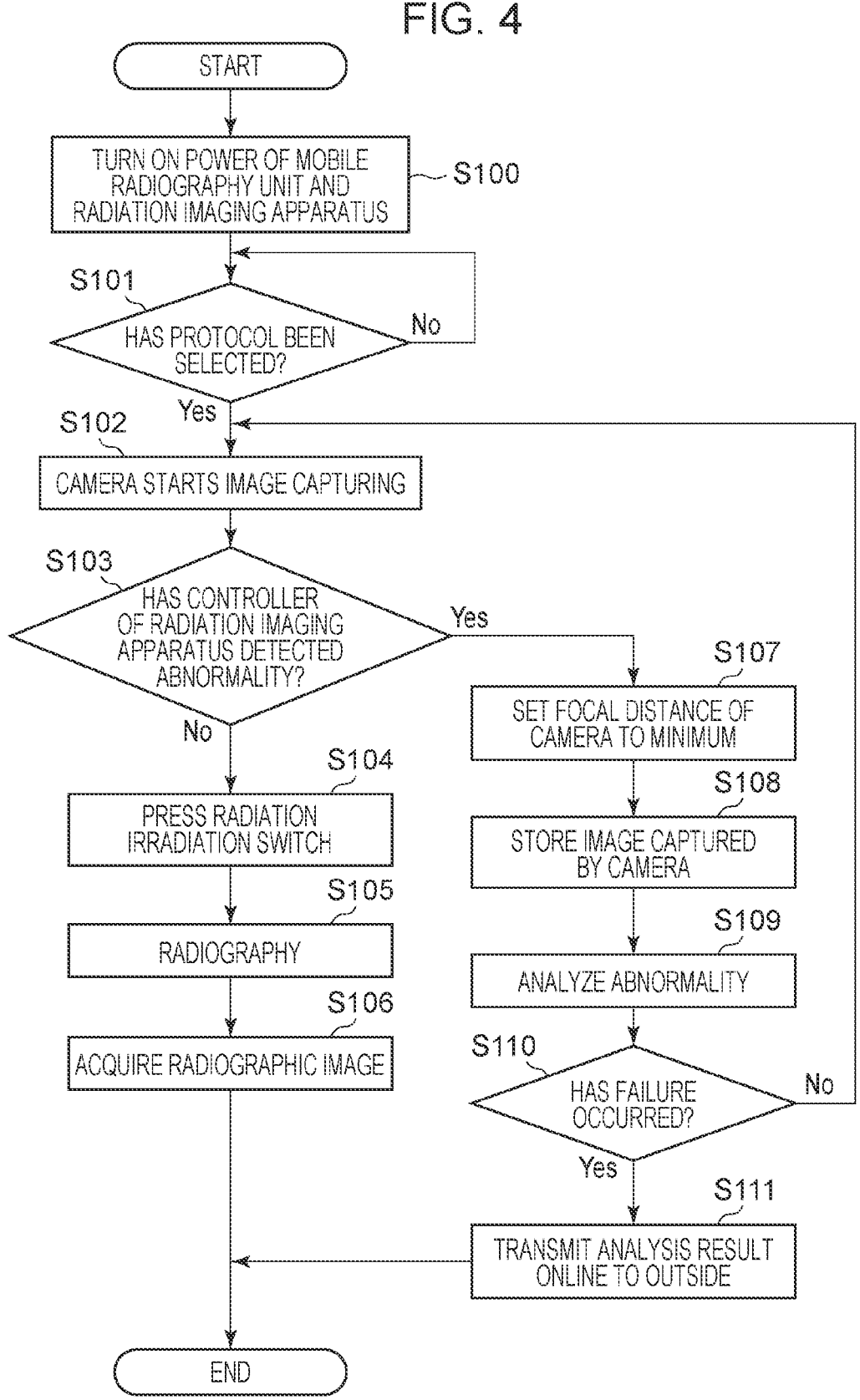

RADIATION IMAGING APPARATUS, RADIATION IMAGING SYSTEM, METHOD, AND NON-TRANSITORY STORAGE MEDIUM

BACKGROUND

Field

The present disclosure relates to a radiation imaging apparatus, a radiation imaging system, a method, and a non-transitory storage medium.

Description of the Related Art

In recent years, radiation imaging apparatuses including a flat panel detector have been widely put into practical use as imaging apparatuses for use in medical image diagnosis or nondestructive inspection using radiation. The flat panel detector includes solid-state imaging elements made of amorphous silicon or single-crystal silicon and arranged in a two-dimensional manner.

These radiation imaging apparatuses store signal charges generated for individual pixels based on the amount of detected radiation, reads and AD-converts the charges, and is thereby capable of acquiring an image. These radiation imaging apparatuses are used, in medical image diagnosis, for example, as a digital imaging apparatus for still image capturing such as general radiography and moving image capturing such as fluoroscopic radiography.

The development of wireless radiation imaging apparatuses has, for example, made the handling of radiation imaging apparatuses easier, increasing the opportunities of being carried, being installed in an operating table or a platform, or being used in a mobile radiography unit. This can cause a failure of a radiation imaging apparatus resulting from, for example, a drop or the like.

The increase in the opportunities of being carried diversifies the environment where the radiation imaging apparatus is used. For example, when there is a medical apparatus that emits magnetic noise, such as a magnetic resonance imaging (MRI) apparatus, an image can be affected by noise or wireless communication can be interrupted, which can result in degrading of usability.

To detect such an abnormality, test image capturing can be performed at regular intervals, and determination made whether a captured image is normal. For example, Japanese Patent Laid-Open No. 2002-277993 discloses a method for statistically processing an analysis value obtained from image information acquired by an imaging apparatus to detect whether the imaging apparatus has an abnormality, and notifying a maintenance center of a detection result.

When the maintenance center is notified of an abnormality in the imaging apparatus, a serviceman collects the imaging apparatus and determines the cause of the abnormality. At this time, rapid determination of the cause makes the abnormality addressed rapidly.

SUMMARY

The present disclosure provides a technique for more rapidly addressing an abnormality occurring in an imaging apparatus.

According to an embodiment of the present disclosure, a radiation imaging apparatus for use in a radiation imaging system includes a radiation source and a camera. The radiation imaging apparatus includes one or more controllers configured to acquire state information of the radiation imaging apparatus and perform, in response to acquisition of state information corresponding to an abnormality of the radiation imaging apparatus, communication to cause the camera to perform image capturing on a range including the radiation imaging apparatus.

Further features of the present disclosure will become apparent from the following description of exemplary embodiments with reference to the attached drawings.

BRIEF DESCRIPTION OF THE DRAWINGS

FIG. 4 is a flowchart illustrating an operation of the radiation imaging system according to the first embodiment.

DESCRIPTION OF THE EMBODIMENTS

Figure 1:
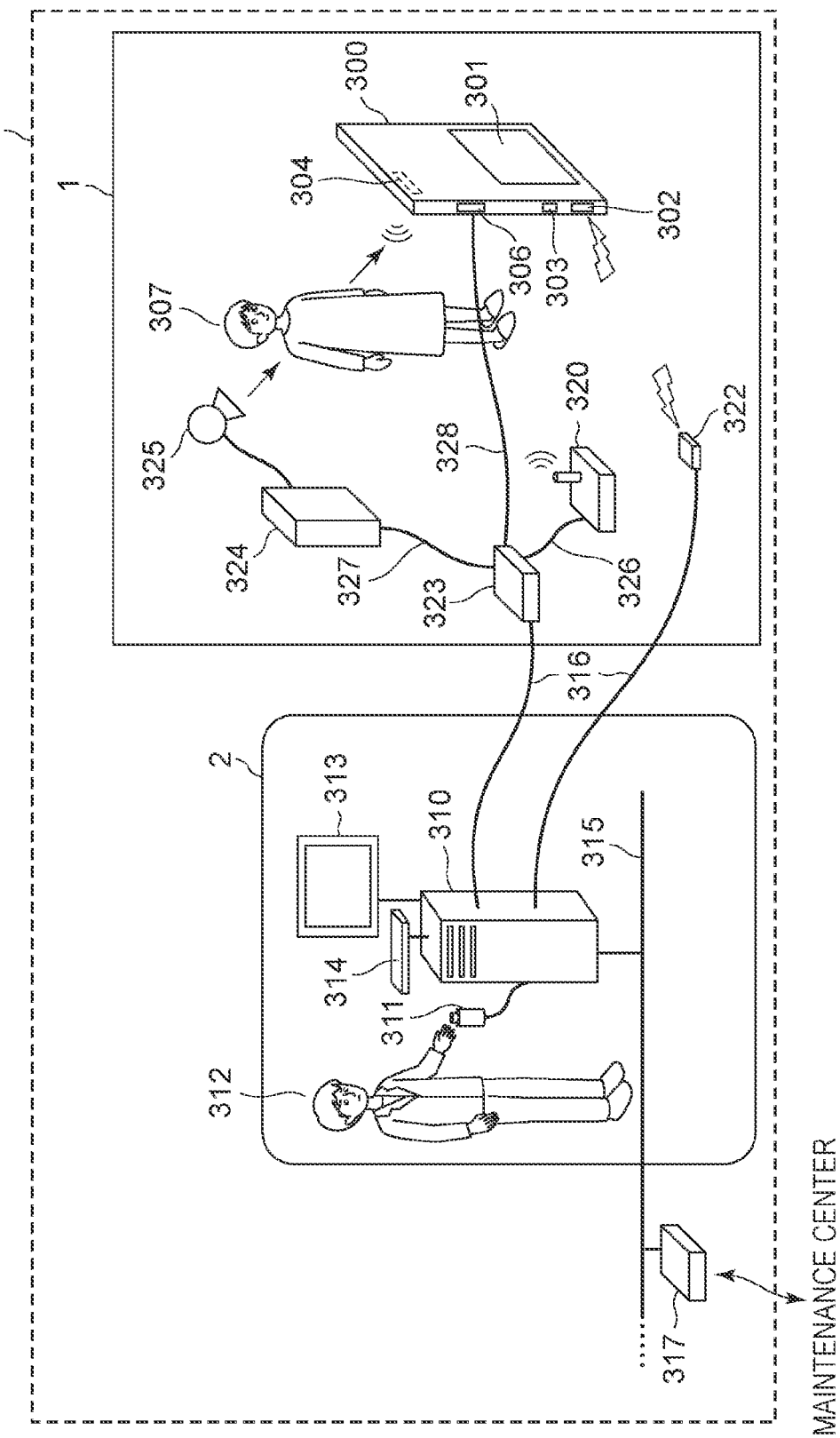
FIG. 1 is a schematic diagram illustrating a radiation imaging system according to a first embodiment.

A radiation imaging system according to a first embodiment will be described with reference to the drawings. FIG. 1 is a diagram illustrating the radiation imaging system according to the first embodiment.

As illustrated in FIG. 1, a radiation imaging system 10 is provided in a radiation room 1 for performing radiography using radiation irradiation, and a control room 2 located near the radiation room 1.

The radiation imaging system 10 includes, in the radiation room 1, a radiation imaging apparatus 300, an access point (AP) 320, a communication control apparatus 323, a radiation generating apparatus 324, and a radiation source 325.

The radiation imaging system 10 also includes, in the radiation room 1, an entry apparatus 322, an AP communication cable 326, a radiation-generating-apparatus communication cable 327, and a sensor communication cable 328.

The radiation imaging system 10 includes, in the control room 2, a control apparatus 310, a radiation irradiation switch 311, a display apparatus 313, an input apparatus 314, an in-hospital local area network (LAN) 315, a hospital local server 317 and radiation-room communication cables 316.

The radiation imaging apparatus 300 includes a power supply controller 301 constituted by a battery or the like, a near-field wireless communication unit 302, a registration switch 303, a wireless communication unit 304, and a wired communication unit 306. The radiation imaging apparatus 300 detects radiation transmitted through a subject 307 and generates radiographic image data.

The access point 320 is an access point for performing wireless communication, and is used for the communication between the radiation imaging apparatus 300 and the control apparatus 310 via the communication control apparatus 323. The communication between the radiation imaging apparatus 300 and the communication control apparatus 323 can be wired communication using the sensor communication cable 328. In the present embodiment, the access point 320 performs communication via, for example, the 2.4 GHz band, the 5 GHz band, or the 6 GHz band of a wireless LAN.

The radiation generating apparatus 324 controls the radiation source 325 to irradiate the subject 307 with radiation.

The radiation generating apparatus 324 controls the radiation source 325 to emit radiation based on a predetermined condition, and controls generation of radiation in response to a signal indicating the start or stop of irradiation received from the radiation imaging apparatus 300.

The AP communication cable 326 is a cable for connecting the access point 320 and the communication control apparatus 323. The radiation-generating-apparatus communication cable 327 is a cable for connecting the radiation generating apparatus 324 and the communication control apparatus 323.

The control apparatus 310 communicates with the radiation generating apparatus 324 and the radiation imaging apparatus 300 via the communication control apparatus 323, and the access point 320 or the sensor communication cable 328, and controls the radiation imaging system 10 in a centralized manner.

The radiation irradiation switch 311 inputs a timing of radiation irradiation in response to an operation performed by an operator 312. The input apparatus 314 is an apparatus that inputs an instruction from the operator 312, and can be an input apparatus of various types, such as a keyboard or a touch screen.

The display apparatus 313 is an apparatus that displays radiographic image data subjected to image processing and a graphical user interface (GUI), and can be a display or the like. The in-hospital LAN 315 is a backbone network in a hospital. The radiation-room communication cables 316 are cables for connecting the control apparatus 310 to the communication control apparatus 323 and the entry apparatus 322 in the radiation room 1.

Next, an operation of the radiation imaging system 10 will be described.

First, the operator 312 performs an operation of registering the radiation imaging apparatus 300 in the radiation imaging system 10. Upon the registration switch 303 of the radiation imaging apparatus 300 being pressed by the operator 312, near-field wireless communication is started between the near-field wireless communication unit 302 of the radiation imaging apparatus 300 and the entry apparatus 322.

The control apparatus 310 transmits wireless connection related information of the access point 320 to the radiation imaging apparatus 300 via the near-field wireless communication of the entry apparatus 322. The wireless connection related information includes, for example, a communication scheme such as IEEE 802.11, a physical channel, SSID, an encryption key, and so forth in the case of a wireless LAN.

The radiation imaging apparatus 300 sets the wireless communication unit 304 based on the received wireless connection related information. As a result of the setting, the radiation imaging apparatus 300 establishes the connection of wireless communication between the access point 320 and the wireless communication unit 304.

The wireless connection related information can be transmitted to the radiation imaging apparatus 300 via the sensor communication cable 328 and the wired communication unit 306.

The operator 312 inputs subject information of the subject 307, such as the ID, name, and date of birth of the subject 307, and an imaging part of the subject 307 to the control apparatus 310. After inputting an imaging part, the operator 312 fixes the position of the subject 307 and the radiation imaging apparatus 300.

After preparation for radiography has been completed, the operator 312 presses the radiation irradiation switch 311. Upon the radiation irradiation switch 311 being pressed, radiation is emitted from the radiation source 325 toward the subject 307.

The radiation imaging apparatus 300 wirelessly communicates with the radiation generating apparatus 324 to control the start or stop of radiation irradiation. The radiation applied to the subject 307 is transmitted through the subject 307 and enters the radiation imaging apparatus 300. The radiation imaging apparatus 300 converts the entered radiation into visible light and then detects the visible light as a radiographic image signal by a photoelectric conversion element.

The radiation imaging apparatus 300 drives the photoelectric conversion element to read out the radiographic image signal, and converts the analog signal into a digital signal by an AD conversion circuit to obtain digital radiographic image data. The obtained digital radiographic image data is transferred from the radiation imaging apparatus 300 to the control apparatus 310 via wireless communication.

The control apparatus 310 performs image processing on the received digital radiographic image data. The control apparatus 310 displays, on the display apparatus 313, a radiographic image based on the processed radiographic image data.

The control apparatus 310 functions as an image processing apparatus and a display control apparatus.

A camera 330 (see FIG. 3) is located on the radiation source 325, and is used to capture an image of the subject 307 and the radiation imaging apparatus 300 and support positioning of the subject 307 and the radiation imaging apparatus 300. The camera 330 includes a wireless communication unit (not illustrated), and wirelessly communicates with the access point 320.

Figure 2:
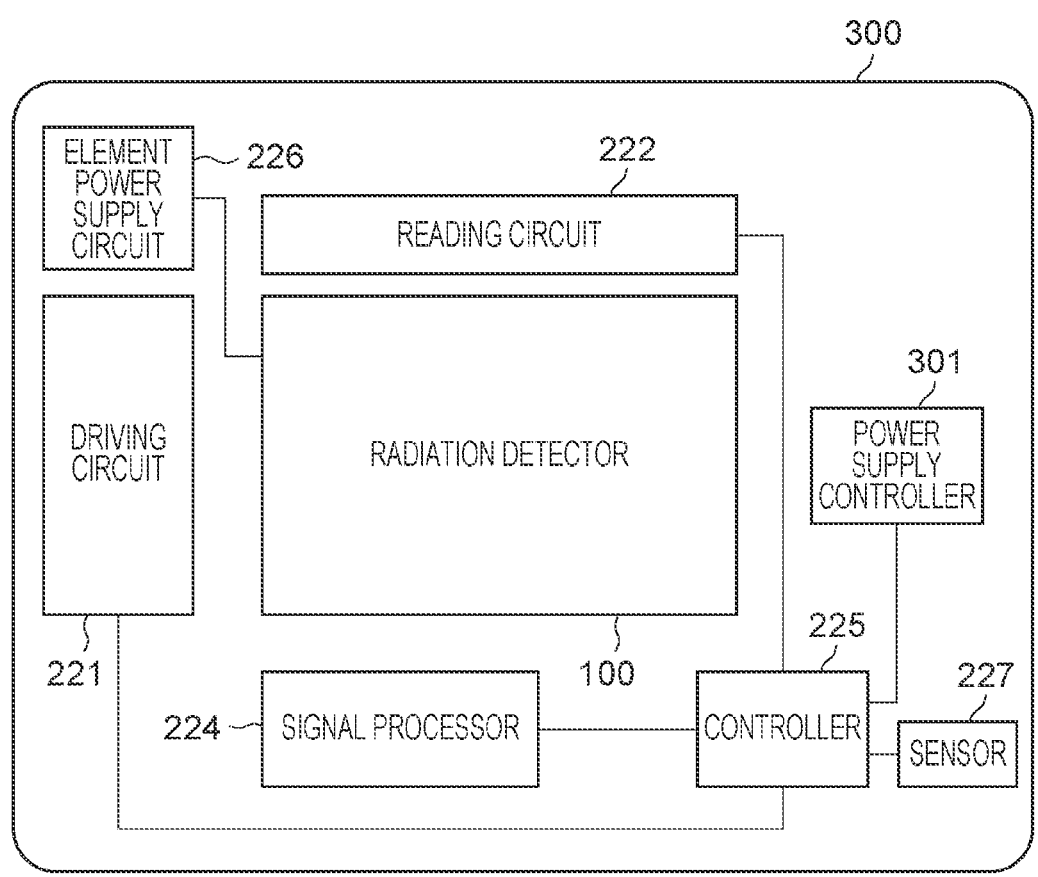
FIG. 2 is a functional block diagram of a radiation imaging apparatus according to the first embodiment.

FIG. 2 is a functional block diagram of the radiation imaging apparatus 300. As illustrated in FIG. 2, the radiation imaging apparatus 300 includes a radiation detector 100. The radiation detector 100 has a function of detecting radiated radiation. The radiation detector 100 includes a plurality of pixels arranged in a plurality of rows and a plurality of columns (not illustrated). In the description below, a region in which the plurality of pixels are arranged in the radiation detector 100 is referred to as an imaging region.

The radiation detector 100 includes a plurality of signal lines and a plurality of drive lines (not illustrated). Each signal line corresponds to one of the plurality of columns in the imaging region. Each drive line corresponds to one of the plurality of rows in the imaging region.

Each signal line is connected to a reading circuit 222. Here, the reading circuit 222 includes a plurality of integral amplifiers, a multiplexer, and an analog-to-digital converter (hereinafter referred to as an AD converter). Each drive line is driven by a driving circuit 221. The radiation detector 100 is connected to the reading circuit 222 and the driving circuit 221 via respective connection lines (not illustrated).

The radiation detector 100 also includes bias lines connected to individual pixels (not illustrated). The bias lines each receive a bias voltage Vs from an element power supply circuit 226. The bias voltage Vs is supplied from the element power supply circuit 226.

The power supply controller 301 is constituted by a battery, a DC/DC converter, and the like. The power supply controller 301 includes the element power supply circuit 226, and generates power for an analog circuit and power for a digital circuit that performs drive control, wireless communication, and so forth. For simple illustration, the power supply controller 301 and the element power supply circuit 226 are separately illustrated in FIG. 2.

A controller 225 controls the driving circuit 221, the reading circuit 222, etc., based on information received from a signal processor 224 or a control command received from the control apparatus 310.

A sensor 227 is a detection unit for detecting a state of the radiation imaging apparatus 300. The sensor 227 is connected to the controller 225, and includes one or more of an acceleration sensor, an angular velocity sensor, a temperature sensor, a current sensor, a voltage sensor, a magnetic sensor, a surface potential sensor, an optical sensor, or a water leakage sensor.

Figure 3:
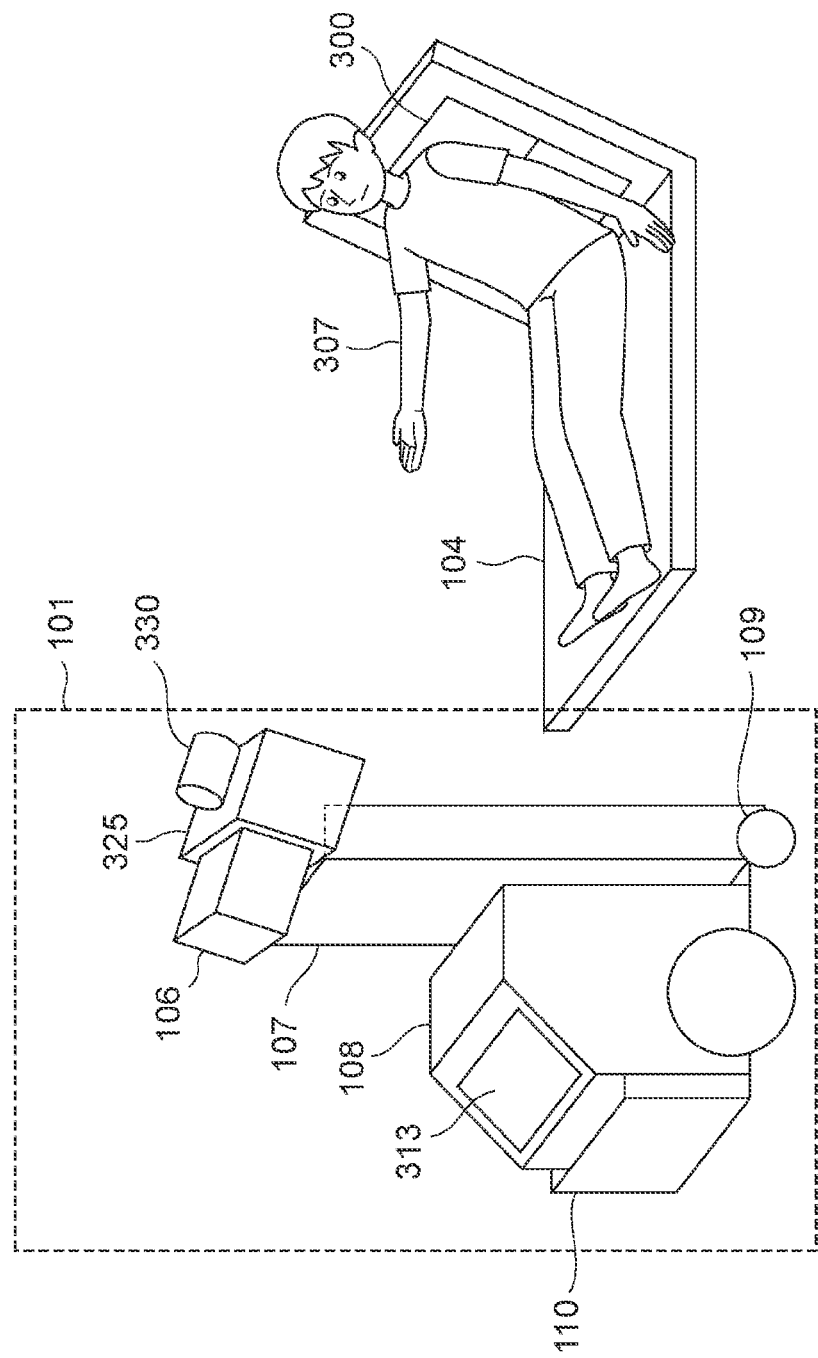
FIG. 3 is a schematic diagram illustrating the radiation imaging system applied to a mobile radiography unit according to the first embodiment.

FIG. 3 is a diagram illustrating an example configuration of a mobile radiography unit that is moved to, for example, a subject's bedside to perform radiography on the subject 307. A mobile radiography unit 101 includes the radiation source 325. The mobile radiography unit 101 is used together with the radiation imaging apparatus 300. The radiation imaging apparatus 300 is placed behind the subject 307, who is located on a bed 104.

In addition to the radiation source 325, the mobile radiography unit 101 includes a first arm 106 that supports the radiation source 325, a second arm 107, a housing 108, a base 109, and a radiation-imaging-apparatus holder 110. The housing 108 has the display apparatus 313 incorporated into it. The housing 108 includes a battery (not illustrated), the radiation generating apparatus 324, the control apparatus 310, and the access point 320.

The display apparatus 313 is constituted by a touch screen and can accept an input from an operator. The display apparatus 313 can employ another input method, and can be a known input device such as a keyboard, a mouse, or a sound recognition device.

Next, an operation performed by the radiation imaging apparatus 300 when an abnormality occurs will be described with reference to FIG. 4 and FIGS. 5A and 5B. FIG. 4 illustrates an operation flow of the apparatus according to the present embodiment. First, in S100, the operator 312 turns on the power of the mobile radiography unit 101 and the radiation imaging apparatus 300. The display apparatus 313, the radiation source 325, the radiation generating apparatus 324, the control apparatus 310, and the access point 320 then begin operating.

Next, in S101, the control apparatus 310 detects whether the operator 312 has selected a radiography protocol using the display apparatus 313 that also functions as an input apparatus. If the control apparatus 310 detects that a radiography protocol has not been selected, S101 is repeated.

If it is detected in S101 that a radiography protocol has been selected, the camera 330 starts image capturing in S102, and the operator 312 performs positioning of the radiation source 325, the radiation imaging apparatus 300, and the subject 307. Based on an image captured by the camera 330, the control apparatus 310 displays an instruction on the display apparatus 313 so that the radiation source 325, the radiation imaging apparatus 300, and the subject 307 face each other, and thereby the operator 312 performs positioning.

In S103, the controller 225 of the radiation imaging apparatus 300 determines whether the radiation imaging apparatus 300 has an abnormality based on an output of the sensor 227.

For example, presume the operator 312 accidentally drops the radiation imaging apparatus 300 while placing the radiation imaging apparatus 300 behind the subject 307 who is on the bed 104. In this example, the controller 225 of the radiation imaging apparatus 300 detects, via the acceleration sensor of the sensor 227, that an acceleration of a predetermined value or more has been applied, and detects an abnormality.

Since the controller 225 detected an abnormality, flow proceeds to S107, where the controller 225 immediately transmits a command for setting the focal distance of the camera 330 to a minimum amount via wireless communication to enable the camera 330 to perform image capturing at a wide angle. The focal distance of the camera 330 is set to the minimum amount to perform image capturing on a range including the radiation imaging apparatus 300 and acquire information about the situation where an abnormality has occurred. In S108, the controller 225 transmits a command for acquiring an image captured by the camera 330 via wireless communication, and acquires the image captured by the camera 330.

Figure 5A:
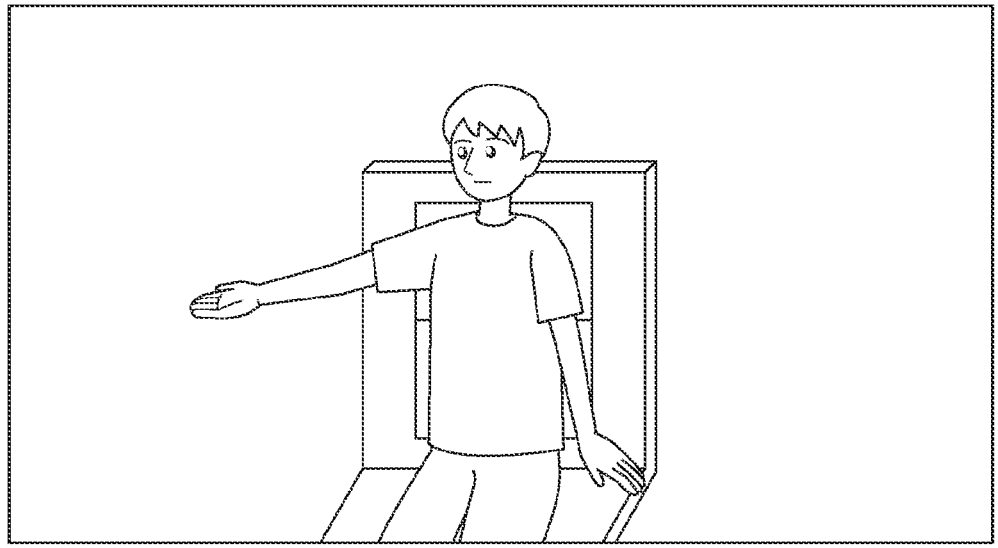
FIGS. 5A and 5B illustrate an image in a normal state and an image in an abnormal state, respectively, captured by a camera according to the first embodiment.
Figure 5B:
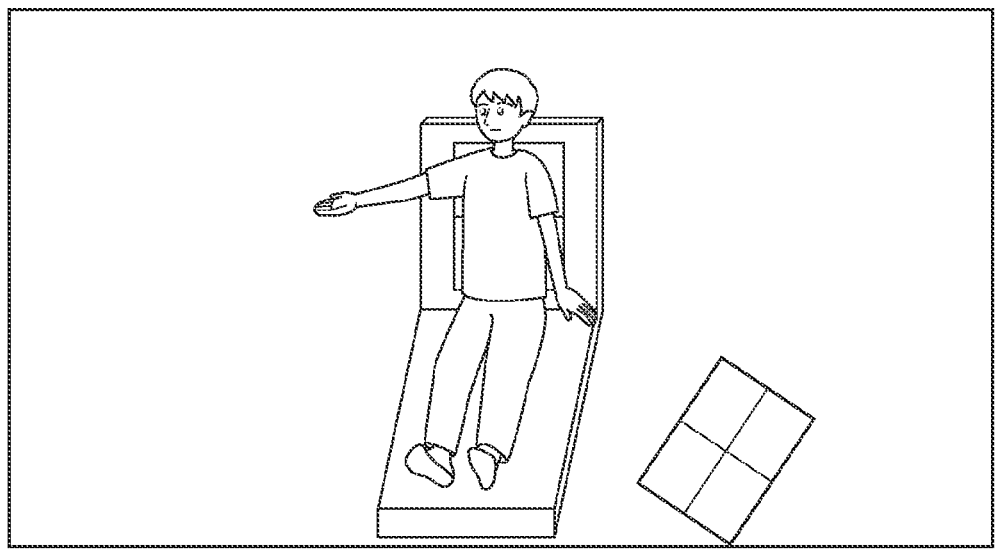

The image capturing by the camera 330 in S102 is performed at a focal distance where the camera 330 has an angle of view such that the subject 307 and the radiation imaging apparatus 300 are mainly photographed, as illustrated in FIG. 5A. However, if the controller 225 detects an abnormality in the radiation imaging apparatus 300 in S103, the focal distance is set to the minimum amount in S107 so that the camera 330 has the largest angle of view, as illustrated in FIG. 5B. Thus, the state where, for example, the radiation imaging apparatus 300 has been dropped can be photographed.

In S109, the controller 225 performs analysis using acquired still image(s) or moving image(s), the details of the detected abnormality, and a self-diagnosis result. In S110, the controller 225 determines whether a failure has occurred in the radiation imaging apparatus 300.

If it is determined in S110 that a failure has occurred, in S111 the controller 225 transmits online the analysis result external to the radiation imaging system 10 (hereinafter referred to as "outside"), such as a maintenance center. The controller 225 can transmit captured data together with the analysis result. The captured data can be either still image(s) or moving image(s).

If the captured data includes the subject 307, a process of obscuring the identity of the subject 307 can be performed to protect the subject's 307 privacy. The controller 225 displays the abnormal state on the display apparatus 313, notifies the operator 312, and causes the operator 312 to cancel any radiography event.

The analysis result can be transmitted to the outside via the control apparatus 310, or can be transmitted directly to the outside by the radiation imaging apparatus 300 using wireless communication or the like.

If it is determined in S110 that no failure has occurred, the process returns to S102, and the positioning of the radiation source 325, the radiation imaging apparatus 300, and the subject 307 is restarted.

After the positioning has ended and preparation for radiography has been completed, the operator 312 presses the radiation irradiation switch 311 in S104. Upon the radiation irradiation switch 311 being pressed, radiation is emitted from the radiation source 325 toward the subject 307, and radiography is performed in S105.

In S106, the radiation imaging apparatus 300 drives the photoelectric conversion element to read a radiographic image signal, converts the analog signal into a digital signal by using the AD conversion circuit, and acquires digital radiographic image data. The acquired digital radiographic image data is transferred from the radiation imaging apparatus 300 to the control apparatus 310 via wireless communication.

In the above-described embodiment, the acceleration sensor detects that an acceleration of a predetermined value or more has been applied to the radiation imaging apparatus 300, and thereby an abnormality is detected. In another exemplary embodiment, an angular velocity sensor can detect that an angular velocity of a predetermined value or more has been applied to the radiation imaging apparatus 300, and thereby an abnormality can be detected. An abnormality detected in this case can be, for example, collision of the radiation imaging apparatus 300 with, for example, something like a wall or the like.

In yet another exemplary embodiment, a temperature sensor can detect that a temperature of a predetermined value or more has been generated in the radiation imaging apparatus 300, and thereby an abnormality can be detected. An abnormality detected in this case can be, for example, a failure of a component in the radiation imaging apparatus 300.

In still yet another exemplary embodiment, a current sensor or voltage sensor can detect that a current or voltage of a predetermined value or more has been generated in the radiation imaging apparatus 300, and thereby an abnormality can be detected. An abnormality detected in this case can be, for example, a failure of a component in the radiation imaging apparatus 300.

In another exemplary embodiment, a surface potential sensor can detect that static electricity of a predetermined value or more has been applied to the radiation imaging apparatus 300, and thereby an abnormality can be detected. An abnormality detected in this case can be, for example, static electricity generated when the operator 312 touches the radiation imaging apparatus 300.

In another exemplary embodiment, an optical sensor such as an optical transistor can detect leakage of light in the radiation imaging apparatus 300, and thereby an abnormality can be detected. An abnormality detected in this case can be, for example, leakage of external light into the radiation imaging apparatus 300 due to, for example, loosening of a screw of the radiation imaging apparatus 300.

In still another exemplary embodiment, a water leakage sensor of a resistance detection scheme or the like can detect leakage of water in the radiation imaging apparatus 300, and thereby an abnormality can be detected. An abnormality detected in this case can be, for example, leakage of water into the radiation imaging apparatus 300 being washed due to loosening of a screw of the radiation imaging apparatus 300.

An abnormality of the radiation imaging apparatus 300 can be detected using known sensors other than those described above.

In the present embodiment, if a determination is made in S110 that a failure has occurred, in S111, the controller 225 transmits online an analysis result to the outside, such as a maintenance center. This implementation is not seen to be limiting. In another exemplary embodiment, for example, if a determination is made in S110 that a failure has occurred, in S111 the controller 225 can display an abnormal state on the display apparatus 313 to notify the operator 312, and the operator 312 can notify the outside, such as a maintenance center.

The camera 330 can be an infrared camera. In this case, an abnormal temperature of the radiation imaging apparatus 300 can be detected from an image captured by the camera 330.

The camera 330 can capture an image of the radiation imaging apparatus 300 in response to detection of a predetermined operation performed by the operator 312 of the radiation imaging apparatus 300 via the display apparatus 313 that also functions as an input apparatus. The predetermined operation can be, for example, inputting of a specific command using a keyboard, pressing of a predetermined button, or an operation using another input apparatus.

As described above, as a result of still image(s) or moving image(s) depicting an abnormal surrounding situation being acquired in addition to information from various sensors provided in the radiation imaging apparatus 300, more detailed information about abnormal situations of the radiation imaging apparatus can be acquired, and abnormalities can be addressed more rapidly.

A second embodiment will now be described. In the first embodiment, a description was provided of an example where the controller 225 of the radiation imaging apparatus 300 detects an abnormality of the radiation imaging apparatus 300. In the second embodiment, a description will be provided of an example where the control apparatus 310 detects an abnormality of the radiation imaging apparatus 300. In the following description, only the differences from the first embodiment will be described.

Figure 6:
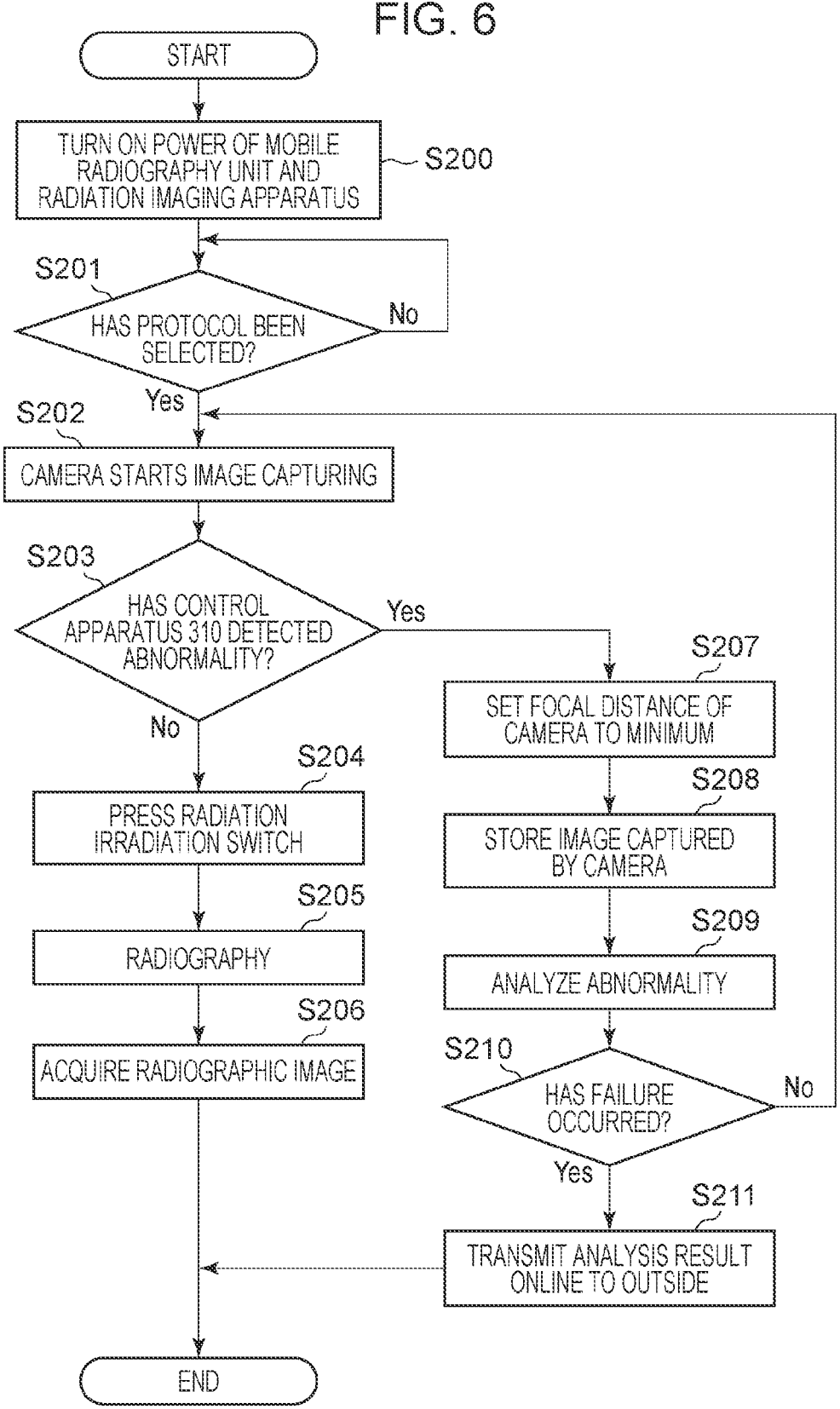
FIG. 6 is a flowchart illustrating an operation of the radiation imaging system according to a second embodiment.

FIG. 6 illustrates an operation flow of the apparatus according to the second embodiment of the present disclosure.

First, in S200, the operator 312 turns on the power of the mobile radiography unit 101 and the radiation imaging apparatus 300. The display apparatus 313, the radiation source 325, the radiation generating apparatus 324, the control apparatus 310, and the access point 320 then begin operating. The radiation imaging apparatus 300 also transmits information of individual sensors acquired from the sensor 227 to the control apparatus 310 at regular intervals.

S201 and S202 are the same as S101 and S102, respectively. In S203, the control apparatus 310 determines whether the information of individual sensors of the sensor 227 received from the radiation imaging apparatus 300 includes an abnormality.

For example, when there is a medical apparatus that emits magnetic noise, such as an MRI apparatus, in the vicinity where the mobile radiography unit 101 has moved, application of magnetism of a predetermined value or more causes an abnormal value to be output from the magnetic sensor of the sensor 227 of the radiation imaging apparatus 300. In response to detecting an abnormality from sensor information, in S207, the control apparatus 310 immediately transmits a command for setting the focal distance of the camera 330 to the minimum amount via wireless communication, and the camera 330 is set to have a wide angle. In S208, the control apparatus 310 transmits a command for performing image capturing with the camera 330 via wireless communication, and causes the camera 330 to acquire still image(s) or moving image(s).

Figure 7A:
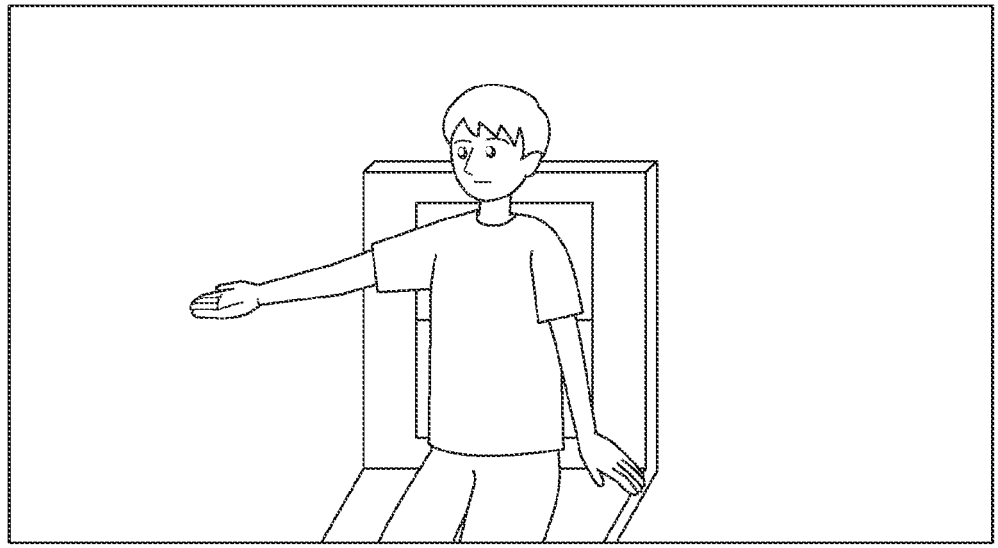
FIGS. 7A and 7B illustrate an image in a normal state and an image in an abnormal state, respectively, captured by a camera according to the second embodiment.
Figure 7B:
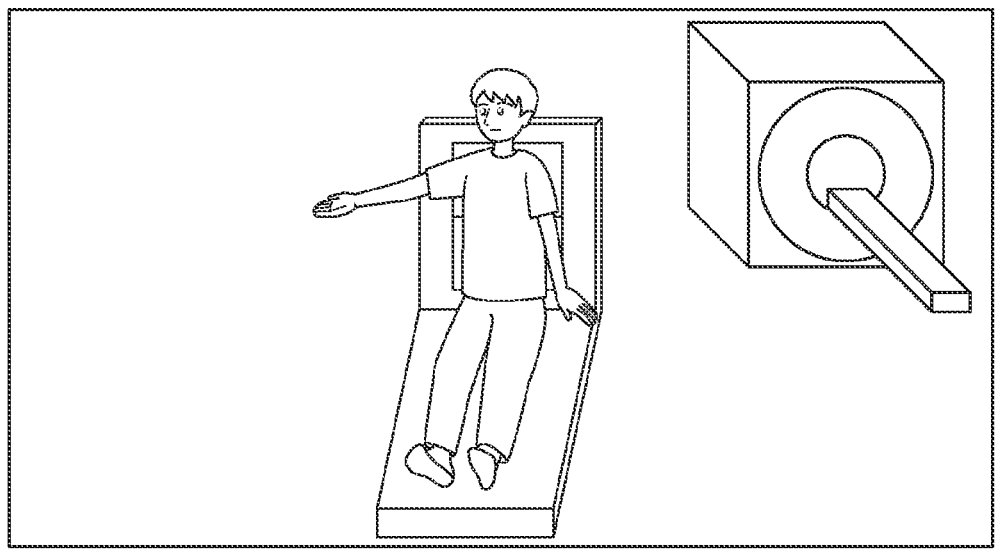

The image capturing by the camera 330 in S202 is performed at a focal distance where the camera 330 has an angle of view such that the subject 307 and the radiation imaging apparatus 300 are mainly photographed, as illustrated in FIG. 7A. If in S203 the control apparatus 310 detects an abnormality in the radiation imaging apparatus 300, the focal distance is set to the minimum in S207 so that the camera 330 has the largest angle of view, as illustrated in FIG. 7B. Thus, the state around the radiation imaging apparatus 300 can be photographed.

In S209, the control apparatus 310 performs analysis using the stored still image(s) or moving image(s), the details of the detected abnormality, and a self-diagnosis result. In S210, the control apparatus 310 determines whether a failure has occurred in the radiation imaging apparatus 300.

If it is determined in S210 that a failure has occurred, in S211 the control apparatus 310 transmits the analysis result to an external maintenance center or the like. The control apparatus 310 can transmit captured still image(s) or moving image(s) together with the analysis result. If it is determined in S210 that no failure has occurred, the process returns to S202, and the positioning of the radiation source 325, the radiation imaging apparatus 300, and the subject 307 is restarted.

S204, S205, and S206 are the same as S104, S105, and S106, respectively. Radiography is performed upon the radiation irradiation switch 311 being pressed, and radiographic image data is transferred to the control apparatus 310 via wireless communication.

In the above-described example, the magnetic sensor detects that magnetism of a predetermined value or more has been applied to the radiation imaging apparatus 300, and an abnormality is detected. In another exemplary embodiment, a component is provided that counts the number of times the wireless communication unit 304 fails in wireless communication and performs retransmission. In this case, it is possible to detect an abnormality caused by magnetic noise, electric noise, or the like, when the number of retransmissions is a predetermined value or more.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2022-188490, filed Nov. 25, 2022, which is hereby incorporated by reference herein in its entirety.

What is claimed is:

1. A radiation imaging apparatus for use in a radiation imaging system including a radiation source and a camera, the radiation imaging apparatus comprising:
one or more controllers configured to:
acquire state information of the radiation imaging apparatus; and
perform, in response to acquisition of state information corresponding to an abnormality of the radiation imaging apparatus, communication to cause the camera to perform image capturing on a range including the radiation imaging apparatus.

2. The radiation imaging apparatus according to claim 1, wherein
the one or more controllers are further configured to:
perform, based on the state information corresponding to the abnormality and image capturing information acquired by the image capturing, analysis of a state of the radiation imaging apparatus; and
transmit a result of the analysis external to the radiation imaging system.

3. The radiation imaging apparatus according to claim 1, wherein
the one or more controllers are further configured to:
set a focal distance of the camera to a minimum amount in the image capturing; and
when a subject is in an image acquired in the image capturing, perform a process of obscuring the identity of the subject.

4. The radiation imaging apparatus according to claim 1, wherein
the one or more controllers are further configured to cause the camera to perform the image capturing in response to detection of a predetermined operation performed by an operator of the radiation imaging apparatus.

5. The radiation imaging apparatus according to claim 1, further comprising:
a sensor configured to acquire the state information,
wherein the sensor is one more of an acceleration sensor, an angular velocity sensor, a temperature sensor, a current sensor, a voltage sensor, a magnetic sensor, a surface potential sensor, an optical sensor, or a water leakage sensor.

6. The radiation imaging apparatus according to claim 1, further comprising:
a wireless communication unit; and
a detector configured to count the number of times information acquired by the image capturing is retransmitted by the wireless communication unit.

7. A radiation imaging system comprising:
a radiation source;
a camera; and
a radiation imaging apparatus,
wherein the radiation imaging apparatus includes one or more controllers configured to:
acquire state information of the radiation imaging apparatus; and
perform, in response to acquisition of state information corresponding to an abnormality of the radiation imaging apparatus, communication to cause the camera to perform image capturing on a range including the radiation imaging apparatus.

8. The radiation imaging system according to claim 7, wherein
the camera is configured to capture one or more of a still image or a moving image.

9. The radiation imaging system according to claim 7, wherein
the camera is configured to provide an image to assist a user in positioning the radiation imaging apparatus.

10. The radiation imaging system according to claim 7, wherein
the camera is an infrared camera.

11. A method for a radiation imaging apparatus for use in a radiation imaging system including a radiation source and a camera, the method comprising:
acquiring state information of the radiation imaging apparatus; and
performing, in response to acquisition of state information corresponding to an abnormality of the radiation imaging apparatus, communication to cause the camera to perform image capturing on a range including the radiation imaging apparatus.

12. The method according to claim 11, further comprising:
analyzing, based on the state information corresponding to the abnormality and image capturing information acquired by the image capturing, a state of the radiation imaging apparatus; and
transmitting a result of the analysis external to the radiation imaging system.

13. A non-transitory storage medium storing a program that when executed causes a radiation imaging apparatus for use in a radiation imaging system including a radiation source and a camera to execute a method, the method comprising:
acquiring state information of the radiation imaging apparatus; and
performing, in response to acquisition of state information corresponding to an abnormality of the radiation imaging apparatus, communication to cause a camera to perform image capturing on a range including the radiation imaging apparatus.

\* \* \* \* \*